US009458196B2

(12) United States Patent
Fnu et al.

(10) Patent No.: US 9,458,196 B2
(45) Date of Patent: Oct. 4, 2016

(54) SYNTHETIC PEPTIDES CAPABLE OF BINDING TO INFLUENZA HEMAGGLUTININ PROTEIN (71) Applicant: COUNCIL OF SCIENTIFIC & INDUSTRIAL RESEARCH, New Delhi (IN)

(72) Inventors: Ashish Fnu, Punjab (IN); Kalpana Pandey, Punjab (IN); Yogendra Singh Rathore, Punjab (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/378,568

(22) PCT Filed: Feb. 14, 2013

(86) PCT No.: PCT/IN2013/000094
§ 371 (c)(1),
(2) Date: Aug. 13, 2014

(87) PCT Pub. No.: WO2013/121441
PCT Pub. Date: Aug. 22, 2013

(65) Prior Publication Data
US 2015/0071952 A1    Mar. 12, 2015

(30) Foreign Application Priority Data
Feb. 14, 2012 (IN) .......................... 0411/DEL/2012

(51) Int. Cl.
C07K 7/60      (2006.01)
C07K 14/11     (2006.01)
A61K 39/145    (2006.01)
C07K 7/06      (2006.01)
C07K 14/005    (2006.01)
C07K 5/113     (2006.01)
C07K 7/08      (2006.01)
C12N 7/00      (2006.01)

(52) U.S. Cl.
CPC .............. *C07K 7/06* (2013.01); *C07K 5/1021* (2013.01); *C07K 7/08* (2013.01); *C07K 14/005* (2013.01); *C12N 7/00* (2013.01); *A61K 39/145* (2013.01); *C12N 2760/16022* (2013.01); *C12N 2760/16033* (2013.01); *C12N 2760/16034* (2013.01)

(58) Field of Classification Search
None
See application file for complete search history.

(56) References Cited

U.S. PATENT DOCUMENTS

| 6,258,527 B1 | 7/2001 | Littman et al. |
| 6,337,181 B1 | 1/2002 | Stewart et al. |
| 2009/0068221 A1 | 3/2009 | Morrison |
| 2011/0150912 A1 | 6/2011 | Perez |

FOREIGN PATENT DOCUMENTS

| DE | 10 2005 060 920 | 6/2007 |
| EP | 2 003 198 | 12/2008 |
| EP | 2 096 121 | 9/2009 |
| WO | WO 2009/133249 | 11/2009 |
| WO | WO 2010/088393 | 8/2010 |
| WO | WO 2011/094357 | 8/2011 |

OTHER PUBLICATIONS

GenBank: BAH30669.1. hemagglutinin, partial [Influenza A virus (A/Gunma/5/2006(H3N2))]. Mar. 31, 2009.*
Gerdon et al. Hemagglutinin linear epitope presentation on monolayer-protected clusters elicits strong antibody binding. Biomacromolecules. Nov.-Dec. 2005;6(6):3419-24.*
International Search Report and Written Opinion issued in corresponding PCT/IN2013/000094, mailed on Aug. 14, 2013.
Bullough et al., *Structure of influenza haemagglutinin at the pH of membrane fusion*, 371 Nature 37-43 (Sep. 1, 1994).
Ekiert et al., *Antibody Recognition of a Highly Conserved Influenza Virus Epitope*, 324 Science 246-251 (Apr. 10, 2009).
Hammel et al., *Solution Structure of Human and Bovine $\beta_2$-Glycoprotein I Revealed by Small-angle X-ray Scattering*, 321 J. Mol. Biol. 85-97 (2002).
Houghten et al., *Effect of Positional Environmental Domains on the Variation of High-Performance Liquid Chromatographic Peptide Retention Coefficients*, 386 Journal of Chromatography 223-228 (1987).
Mertens et al., *Structural characterization of proteins and complexes using small-angle X-ray solution scattering*, 172 Journal of Structural Biology 128-141 (2010).
Sui et al., *Structural and functional bases for broad-spectrum neutralization of avian and human influenza a viruses*, 16(3) Nature Structural & Molecular Biology 265-273 (Mar. 2009).
White et al., *Anti-Peptide Antibodies Detect Steps in a Protein Conformational Change: Low-pH Activation of the Influenza Virus Hemagglutinin*, 105 (No. 6, Pt. 2) The Journal of Cell Biology 2887-2896 (Dec. 1987).
Wilson et al., *The Structure of an Antigenic Determinant in a Protein*, 37 Cell 767-778 (Jul. 1984).

* cited by examiner

*Primary Examiner* — Nick Zou
(74) *Attorney, Agent, or Firm* — Buchanan Ingersoll & Rooney PC (57) ABSTRACT The invention provides peptides capable of binding with influenza hemagglutinin (HA) protein blocking pH-induced shape change or aggregation of the influenza hemagglutinin (HA) protein. The invention also provides a druggable site in influenza Hemagglutinin protein, said druggable site comprises peptide sequences comprising conserved residues.

14 Claims, 5 Drawing Sheets

SEQUENCE LISTING

```
<160> NUMBER OF SEQ ID NOS: 25

<210> SEQ ID NO 1
<211> LENGTH: 8
<212> TYPE: PRT
<213> ORGANISM: Artificial seq
<220> FEATURE:
<223> OTHER INFORMATION: PF11:Peptide binding to HA trimer
```

```
<400> SEQUENCE: 1

Pro Tyr Asp Val Pro Asp Tyr Glu
1               5

<210> SEQ ID NO 2
<211> LENGTH: 8
<212> TYPE: PRT
<213> ORGANISM: Artificial seq
<220> FEATURE:
<223> OTHER INFORMATION: PF12:Peptide binding to HA trimer

<400> SEQUENCE: 2

Pro Tyr Asp Val Pro Asp Tyr Ala
1               5

<210> SEQ ID NO 3
<211> LENGTH: 8
<212> TYPE: PRT
<213> ORGANISM: Artificial seq
<220> FEATURE:
<223> OTHER INFORMATION: PF13:Peptide binding to HA trimer

<400> SEQUENCE: 3

Pro Gly Asp Phe Asn Asp Tyr Glu
1               5

<210> SEQ ID NO 4
<211> LENGTH: 10
<212> TYPE: PRT
<213> ORGANISM: Artificial seq
<220> FEATURE:
<223> OTHER INFORMATION: PF31:Peptide binding to HA trimer

<400> SEQUENCE: 4

Thr Lys Arg Ser Gln Gln Thr Val Ile Pro
1               5                   10

<210> SEQ ID NO 5
<211> LENGTH: 10
<212> TYPE: PRT
<213> ORGANISM: Artificial seq
<220> FEATURE:
<223> OTHER INFORMATION: PF32:Peptide binding to HA trimer

<400> SEQUENCE: 5

Thr Ser Arg Ser Gln Gln Thr Val Ile Pro
1               5                   10

<210> SEQ ID NO 6
<211> LENGTH: 9
<212> TYPE: PRT
<213> ORGANISM: Artificial seq
<220> FEATURE:
<223> OTHER INFORMATION: PF41:Peptide binding to HA trimer

<400> SEQUENCE: 6

Lys Glu Phe Ser Glu Val Glu Gly Arg
1               5

<210> SEQ ID NO 7
<211> LENGTH: 9
<212> TYPE: PRT
<213> ORGANISM: Artificial seq
<220> FEATURE:
<223> OTHER INFORMATION: PF42:Peptide binding to HA trimer
```

```
<400> SEQUENCE: 7

Lys Glu Phe Asn Asn Leu Glu Lys Arg
1               5

<210> SEQ ID NO 8
<211> LENGTH: 14
<212> TYPE: PRT
<213> ORGANISM: Artificial seq
<220> FEATURE:
<223> OTHER INFORMATION: LPF54:Peptide binding to HA trimer

<400> SEQUENCE: 8

Ala Glu Arg Pro Lys Val Arg Gly Gln Ala Gly Arg Met Asn
1               5                   10

<210> SEQ ID NO 9
<211> LENGTH: 12
<212> TYPE: PRT
<213> ORGANISM: Artificial seq
<220> FEATURE:
<223> OTHER INFORMATION: PF21

<400> SEQUENCE: 9

Gly Val His His Pro Gly Thr Asp Asn Asp Gln Ile
1               5                   10

<210> SEQ ID NO 10
<211> LENGTH: 12
<212> TYPE: PRT
<213> ORGANISM: Artificial seq
<220> FEATURE:
<223> OTHER INFORMATION: PF22

<400> SEQUENCE: 10

Gly Val His His Pro Ser Thr Asp Ser Asp Gln Thr
1               5                   10

<210> SEQ ID NO 11
<211> LENGTH: 12
<212> TYPE: PRT
<213> ORGANISM: Artificial Seq
<220> FEATURE:
<223> OTHER INFORMATION: PF23

<400> SEQUENCE: 11

Gly Val His His Pro Ser Asn Glu Thr Glu Gln Arg
1               5                   10

<210> SEQ ID NO 12
<211> LENGTH: 10
<212> TYPE: PRT
<213> ORGANISM: Artificial Seq
<220> FEATURE:
<223> OTHER INFORMATION: PF33

<400> SEQUENCE: 12

Ser Ser Asn Tyr Asn Arg Arg Phe Thr Pro
1               5                   10

<210> SEQ ID NO 13
<211> LENGTH: 10
<212> TYPE: PRT
<213> ORGANISM: Artificial Seq
<220> FEATURE:
<223> OTHER INFORMATION: PF51

<400> SEQUENCE: 13
```

Arg Pro Lys Val Arg Asp Gln Glu Ser Arg
1               5                   10

<210> SEQ ID NO 14
<211> LENGTH: 10
<212> TYPE: PRT
<213> ORGANISM: Artificial Seq
<220> FEATURE:
<223> OTHER INFORMATION: PF52

<400> SEQUENCE: 14

Arg Pro Trp Val Arg Gly Val Ser Ser Arg
1               5                   10

<210> SEQ ID NO 15
<211> LENGTH: 10
<212> TYPE: PRT
<213> ORGANISM: Artificial Seq
<220> FEATURE:
<223> OTHER INFORMATION: PF53

<400> SEQUENCE: 15

Arg Pro Trp Val Arg Gly Leu Ser Ser Arg
1               5                   10

<210> SEQ ID NO 16
<211> LENGTH: 10
<212> TYPE: PRT
<213> ORGANISM: Artificial seq
<220> FEATURE:
<223> OTHER INFORMATION: PF54

<400> SEQUENCE: 16

Arg Pro Lys Val Arg Gly Gln Ala Gly Arg
1               5                   10

<210> SEQ ID NO 17
<211> LENGTH: 14
<212> TYPE: PRT
<213> ORGANISM: Artificial Seq
<220> FEATURE:
<223> OTHER INFORMATION: LPF52

<400> SEQUENCE: 17

Gly Ser Arg Pro Trp Val Arg Gly Val Ser Ser Arg Ile Ser
1               5                   10

<210> SEQ ID NO 18
<211> LENGTH: 14
<212> TYPE: PRT
<213> ORGANISM: Artificial seq
<220> FEATURE:
<223> OTHER INFORMATION: MPF24

<400> SEQUENCE: 18

Ile Trp Gly Val Ala Ala Pro Gly Thr Ala Ala Ala Gln Ile
1               5                   10

<210> SEQ ID NO 19
<211> LENGTH: 16
<212> TYPE: PRT
<213> ORGANISM: Artificial seq
<220> FEATURE:
<223> OTHER INFORMATION: MPF26

<400> SEQUENCE: 19

```
Ile Trp Gly Val Ala Ala Pro Ser Thr Ala Ser Ala Gln Thr Ser Leu
1               5                   10                  15

<210> SEQ ID NO 20
<211> LENGTH: 10
<212> TYPE: PRT
<213> ORGANISM: Artificial seq
<220> FEATURE:
<223> OTHER INFORMATION: MPF51

<400> SEQUENCE: 20

Ala Pro Ala Val Ala Ala Gln Ala Ser Ala
1               5                   10

<210> SEQ ID NO 21
<211> LENGTH: 4
<212> TYPE: PRT
<213> ORGANISM: Influenza virus:HA trimer Chain A, Drug site (120-123)

<400> SEQUENCE: 21

Asp Val Pro Asp
1

<210> SEQ ID NO 22
<211> LENGTH: 6
<212> TYPE: PRT
<213> ORGANISM: Influenza virus:HA trimer Chain A, Drug site (234-240)

<400> SEQUENCE: 22

Arg Ser Gln Gln Thr Val
1               5

<210> SEQ ID NO 23
<211> LENGTH: 10
<212> TYPE: PRT
<213> ORGANISM: Influenza virus:HA trimer Chain A, Drug site (208-217)

<400> SEQUENCE: 23

Val His His Pro Gly Thr Asp Asn Asp Gln
1               5                   10

<210> SEQ ID NO 24
<211> LENGTH: 8
<212> TYPE: PRT
<213> ORGANISM: Influenza virus:HA trimer Chain B, Drug site (247-254)

<400> SEQUENCE: 24

Pro Lys Val Arg Asp Gln Glu Ser
1               5

<210> SEQ ID NO 25
<211> LENGTH: 5
<212> TYPE: PRT
<213> ORGANISM: Influenza virus:HA trimer Chain B, Drug site (441-445)

<400> SEQUENCE: 25

Phe Ser Glu Val Glu
1               5
```

SYNTHETIC PEPTIDES CAPABLE OF BINDING TO INFLUENZA HEMAGGLUTININ PROTEIN

CROSS-REFERENCE TO RELATED APPLICATIONS

This application is a U.S. National Stage patent application pursuant to 35 U.S.C. §371 of International Patent Application PCT/IN2013/000094, filed on Feb. 14, 2013, and published as WO 2013/121441 on Aug. 22, 2013, which claims priority to India Patent Application No. 0411/DEL/2012, filed on Feb. 14, 2012, the content of each is hereby expressly incorporated by reference in their entireties for all purposes.

FIELD OF THE INVENTION

The present invention relates to synthetic peptides capable of binding to influenza hemagglutinin (HA) protein and blocking the pH-induced shape change/aggregation of the hemagglutinin (HA) protein. The invention also relates to a solution structural model of influenza hemagglutinin trimer having full glycosylation to identify a novel druggable site.

BACKGROUND OF THE INVENTION

Influenza, an old world virus is responsible for unpredictable periodic pandemics and seasonal outbreaks, and imposes severe burden on public health. With time, geographic spread of influenza virus has increased. Most importantly, cross-species infective capacity of this virus has led to emergence of newer strains from random gene assortments (1). This peculiar feature categorizes it as one of the deadliest virus. In absence of a generic broad spectrum therapy against influenza strains, different approaches are being formulated including using viral components as vaccine, molecules capable of derailing essential pathways of this virus, besides screening of small molecules based on sialic acid moieties to act as receptor mimics. Interestingly, though influenza is known to evolve via gene reassortment to evade immune system and drugs reactive to its surface components, but host cell entry protocol of this old world virus has remained unchanged (2). A pivotal point in the different events in the influenza infection, endosomal entry, fusion with host membranes, integration with host genetic material for replication and packaging of pro-viral particles for further infection is the low pH induced opening of the HA trimer. HA, an envelope protein on viral surface, is packed as a trimer which opens-up upon sensing low pH, an essential event for viral entry (3). The functional relevance of HA entails it to be a better therapeutic target than the other surface expressed viral molecules. But being variable in nature, the molecules and/or antibodies developed against HA exhibit strain dependence (4).

Importantly, structural data available for HA has remained devoid of the information of carbohydrate/sugar moieties associated with this molecule (2). Electron microscopic details with intact virus suggest 25-35% occupancy of the total viral surface by HA. HA glycoprotein exists as spikes of approximate length 137 Å (5). Functionally, HA belongs to class I fusion protein and type I TM class. Class I fusion protein defines as fusion mediated by conformational changes in the protein and type I TM class represent receptor binding as well as fusion ability of the protein (6). Initially, HA is expressed as an inactive precursor molecule, HA0, which is then converted into active, fusion prone pH sensitive molecule by the host enzyme (7). Intriguingly, nature has encoded dual activity in HA, pH sensing based activation and binding to receptor, and to overcome two barriers before releasing its genetic material into host cell (8). On encountering low pH, the inner part of the HA molecule undergoes loop to helix transition resulting in dislocation of the fusion peptide by ~100 Å towards target membrane for effective viral fusion (3). Irrespective of the fact that HA is a glycosylated entity and is crucial for viral entry, none of the structural studies provides information of the physiologically relevant glycosylated version. The lack of structural information related to glycosylated HA limits the development of anti-influenza drugs/molecules which can target influenza virus via HA molecule.

In current scenario, the evolution of drug resistant strains against FDA approved drugs is alarming (9,10). To overcome the barrier of strain dependence and fast pace of viral evolution there is a need to develop newer target sites and drug molecules. Status of anti-flu drug development with respect to HA has pitfalls like use of monomer of the molecule as template, use of non-glycosylated crystal structure as start point for drug design/screening and strain dependence (4). To overcome these barriers a novel target site needs to be identified in glycosylated HA molecule. Details in the field of anti-influenza therapy clearly suggests the need for identification of a target site in the glycosylated HA molecule and for small molecules capable of blocking the shape changes responsible for viral-host membrane fusion. The invention disclosed here provides a way to fulfill these needs.

OBJECT OF THE INVENTION

The main objective of the invention is to provide peptide capable of binding with influenza hemagglutinin (HA) protein and blocking pH-induced shape change or aggregation of the influenza hemagglutinin (HA) protein.

Another objective of the invention is to provide a solution structural model of influenza hemagglutinin trimer having full glycosylation to identify a novel druggable site and design peptides reactive to this drug site

SUMMARY OF THE INVENTION

The invention provides peptides capable of binding with influenza hemagglutinin (HA) protein and blocking pH-induced shape change or aggregation of the influenza hemagglutinin (HA) protein. The peptide of the invention acts in a strain independent manner. The invention also provides a druggable site in influenza Hemagglutinin protein, said druggable site comprises peptide sequences represented by SEQ ID NO. 21-25.

BRIEF DESCRIPTION OF THE DRAWINGS AND TABLES

FIG. 1. represents SAXS based tracking of increase in particle size of the HA trimer as a function of lowering of buffer pH. In absence of a host membrane, at low pH the fusogenic apparatus of the HA protein is exposed, resulting in the formation of oligomers of high molecular weight which is tracked using SAXS. Increase in the dimension of H1N1 HA trimer as a function of lowering of buffer pH. The interpretations are made by analyzing solution X-ray scattering data. Importantly, this diagram provides unambiguous evidence that the HA protein is trimeric and follows pH induced shape change which leads to aggregation of this protein in low pH conditions. Similar profile is experimentally observed for HA proteins from other influenza strains: H5N1, H9N2, H3N2 and H14N5. Of these, H1N1, H5N1 and H9N2 represent Group 1, whereas H3N2 and H14N5 classify in Group 2 of influenza strains.

FIG. 4 shows view of the drug site systematically identified, in this invention. Left panel shows front view of the druggable pocket (white box shows the pocket identified in HA trimer) whereas right panel shows top view of the HA trimer with arrows indicating the pocket openings. The left panel shows the modeling of the glycosylated form of HA trimer which best-fits the SAXS-data based experimentally measured shape and volume profile. Middle panel shows the top view of the site identified from bioinformatics, molecular modeling and normal mode analysis protocols. This site is composed of conserved residues and plays integral role in the dynamic opening and closing of HA trimer. The zoomed-in view (right panel) shows the druggable site where the third chain has been removed for clarity. A top view shows how the druggable site exists on three sides of the HA trimer. The Table 1 has the sequences of the interchain segments which compose the druggable site.

Table 1 summarizes the sequences of the interchain segments which compose the drug site in influenza Hemagglutinin protein. Residue numbers from the primary structure are mentioned in superscript.

Table 2 summarizes the different peptide sequences which are synthesized by the inventors and are used for in-vitro screening of peptides capable of blocking pH-induced opening of HA trimers from different influenza strains. The ability to block pH-induced changes is mapped qualitatively by estimating the dimensions of the particle size in solution relative to the samples lacking any peptide. The inventors identified eight preferred peptides represented as PF11, PF12, PF13, PF31, PF32, PF41, PF42 and LPF54 showing ability to block pH triggered shape changes in HA proteins from five different viral strains H1N1, H5N1, H9N2, H3N2 and H14N5. The symbols +, ++, +++ and − represent low activity (i.e. 0-33% increment in SAXS based length), moderate activity (33-66% increment in SAXS based length), good activity (66-100% increment in SAXS based length) and inactive peptides respectively.

DETAILED DESCRIPTION OF THE INVENTION

As used herein, "SAXS" refers to small angle X-ray scattering method used to study predominant solution structure of a molecule.

As used herein, "scattering shape" refers to the shape of the molecule which leads to a particular scattering profile.

As used herein, "druggable site" refers to a surface which after reacting with drug molecule will stop viral entry and proliferation.

As used herein, "physiologically relevant" refers to a state which best or closely represents physiological conditions.

As used herein, "aggregate or associate" refers to multimeric association which occurs in the HA protein under low pH conditions.

As used herein, "effective amount" refers to the amount of peptide that carries out or is sufficient to achieve the desired biological activity. One skilled in the art will be able to determine an effective amount through routine experimentation.

As used herein, "vector" refers to a DNA molecule serving as a vehicle capable of carrying exogenous genes into host cells. Preferably, a vector should be able to replicate, have a system for introducing itself into a host cell and should have selectable markers. Also, preferably, a vector should be able to express the DNA molecule and encode the peptide sequence.

As used herein, "pharmaceutically acceptable" refers to a material such as carrier or additives, which does not abrogate the biological activity or properties of any of the components of the composition or vaccine.

As used herein, "carrier" refers to relatively non-toxic chemical compounds or agents that facilitate the incorporation of a compound into cells or tissues.

Influenza remains a biomedical challenge since outbreak size, timings and prime sub-strain of pathogenic virus remains unpredictable due to gene assortment which occurs when the virus resides in different species. This invention aims at developing small peptides/mimetics with anti-influenza potency in a strain independent manner.

Accordingly, the invention provides peptides capable of binding to influenza hemagglutinin trimeric protein and blocking its low pH induced shape change or aggregation. As designed and screened, these peptides act by binding to epitope conserved in the HA trimer of pathogenic influenza and block their low pH sensed opening and entry into host cells for replication. These peptides and their analogs or variants block the low pH induced opening of HA trimer in a strain independent manner which is essential for fusion of the HA protein with its receptors in the endosome of host cells.

In this direction, the inventors prepared a physiologically relevant structure of HA trimer. Though this protein is a glycoprotein, its structures have been solved only in deglycosylated form and crystal structures do not aid in realizing the dynamic nature of the HA protein. So, the inventors acquired solution SAXS data on HA trimeric protein from different strains of influenza. A person skilled in the art would appreciate that it is possible to perform this study using various strains of influenza. For the current study inventors identified and used five different strains of influenza, namely H1N1, H5N1, H9N2, H3N2 and H14N5 and constructed their scattering shapes. Within these shape constraints, the inventors modeled residue-level structures using similarity based methods and placed glycosylation moieties, scattering data and known mass values as reference. Moreover, the pH variation showed aggregation of the trimeric protein indicating that these proteins are correctly folded post-excision from the viral surface. By analyzing the pathogenic influenza database within the shape profiles of this structure, the inventors identified a zone formed by interchain contacts and composed of conserved residues lacking propensity to glycosylation. The zone identified by the inventors comprises small peptide sequences conserved among different influenza strains. Thus, the zone is capable of being used as a druggable site.

Accordingly, the invention provides a druggable site comprising peptide sequences represented by SEQ ID NO. 21-25. Table 1 provides the sequence of interchain segments of the druggable site.

TABLE 1

| Chain A | Chain B |
|---|---|
| Seq ID 21: $D^{120}VPD^{123}$ | Seq ID 24: $P^{247}KVRDQES^{254}$ |
| Seq ID 22: $R^{234}SQQTV^{240}$ | Seq ID 25: $F^{441}SEVE^{445}$ |
| Seq ID 23: $V^{208}HHPGTDNDQ^{217}$ | |

Inventors designed and synthesized peptide sequences which are capable of interacting with any of the sequences selected from SEQ ID NO. 21-25 and are capable of blocking the pH induced shape change of influenza hemagglutinin (HA) protein.

Accordingly, an embodiment of the invention provides a peptide capable of binding with the peptide sequence of influenza hemagglutinin (HA) protein represented by SEQ ID NO. 21-25, wherein the peptide is capable of blocking pH-induced shape change or aggregation of the influenza hemagglutinin (HA) protein.

The peptide of the invention blocks the low pH-induced opening of influenza hemagglutinin (HA) trimer protein.

In a preferred embodiment, the peptides of the invention acts in a strain independent manner. The peptides of the invention are synthetic peptides.

In a preferred embodiment, the peptide of the invention is selected from a group comprising SEQ ID NO: 1-8. Said peptide includes its analogs and variants as well.

Another embodiment of the invention provides a composition comprising one or more of the peptide capable of binding with one or more of the peptide sequence of influenza hemagglutinin (HA) protein represented by SEQ ID. NO. 21-25 and capable of blocking pH-induced shape change or aggregation of the influenza hemagglutinin (HA) protein along with pharmaceutically acceptable additives and carriers.

Yet another embodiment of the invention provides an influenza vaccine comprising one or more of the peptide capable of binding with one or more of the peptide sequence of influenza hemagglutinin (HA) protein represented by SEQ ID NO. 21-25 and capable of blocking pH-induced shape change or aggregation of the influenza hemagglutinin (HA) protein as an active ingredient.

One more embodiment of the invention provide an antibody that recognizes any of the peptide sequence represented by SEQ ID NO. 21-25. Preferably, the antibody and has a protective effect against influenza virus.

Another embodiment of the invention provides a kit comprising one or more of the peptide capable of binding with one or more of the peptide sequence of influenza hemagglutinin (HA) protein represented by SEQ ID NO. 21-25 and capable of blocking pH-induced shape change or aggregation of the influenza hemagglutinin (HA) along with an instructions manual and optionally along with additives and carriers. Said kit is useful for treatment of diseases caused by influenza virus.

Another embodiment of the invention provides a method of treatment of diseases caused by influenza virus, said method comprising administering to the subject in need the effective amount of peptide as claimed in claim 1 or a composition or conjugate comprising said peptide.

In a preferred embodiment, the peptide is administered using biodegradable nanoparticles. The peptide can be administered by Intravenous intramuscular, spinal, epidural, transdermal, subcutaneous, parenteral, intranasalmucosal, oral or rectal route.

The peptide of the invention and/or a composition comprising said peptide is effective in the treatment of organisms selected from the group comprising humans, captive animals, birds and poultry.

For the purpose of the method of treatment, the peptide is used singly or in combination.

Another embodiment of the invention provides use of peptide capable of binding with peptide sequence of influenza hemagglutinin (HA) protein represented by SEQ ID NO. 21-25 for treatment of diseases caused by influenza virus.

Another embodiment of the invention provides a nucleotide sequence encoding the amino acid sequence of the peptide capable of binding with one or more of the peptide sequence of influenza hemagglutinin (HA) protein represented by SEQ ID NO. 21-25 and capable of blocking pH-induced shape change or aggregation of the influenza hemagglutinin (HA) protein.

Another embodiment of the invention provides a vector comprising the nucleotide sequence encoding the peptide of the invention.

Yet another embodiment of the invention provides a druggable site in influenza Hemagglutinin protein, said druggable site comprising the peptide sequences represented by SEQ ID NO. 21-25.

The druggable site of the invention is useful for screening anti influenza/flu drugs.

Another embodiment of the invention provides use of influenza hemagglutinin (HA) protein as a drug target site, wherein said influenza Hemagglutinin protein comprises the peptide sequences represented by SEQ ID NO. 21-25.

Yet another embodiment of the invention provides use of influenza hemagglutinin (HA) protein for screening of potential anti-influenza drugs, wherein said influenza Hemagglutinin protein comprises the peptide sequences represented by SEQ ID NO. 21-25.

An embodiment of the invention provides a method for the preparation of peptides as claimed in claim 1 comprising the steps:
a. subjecting Hemagglutinin protein to SAXS analysis,
b. generating solution scattering based dummy residue model using the scattering data obtained in step (a).
c. comparing solution based model obtained in step (b) with homology based model generated for the protein used for scattering analysis to identify percentage glycosylation.
d. overlaying the solution model and the percentage glycosylation obtained from step (c) on the structure of hemagglutinin to identify glycosylation sites,
e. obtaining glycosylation locations from step (d), wherein computational glycosylation is performed on homology based model to fit the solution structure obtained in step (b) and obtaining representative model,
f. performing multiple sequence analysis of all pathogenic sequences to identify conserved residues after obtaining representative model from step (e),
g. mapping the residues identified in step (f) onto the structure obtained from step (e),
h. identifying residues using model generated in step (f) from adjacent chains which are involved in maintaining chain-chain contacts,
i. identifying a pocket which remains conserved, unglycosylated, surface exposed and involved in maintaining interchain contacts from the information obtained from steps (f), (g) and (h).
j. identifying a druggable site in the head region of the glycosylated hemagglutinin trimer using the steps (a)-(i),
k. deriving peptide sequences forming the pocket based on pocket identified in step (j),
l. synthesizing peptides complementary to the sequences obtained in step (k), using solid phase peptide synthesis on 2-Cl trityl beads using F-moc chemistry,
m. executing chain elongation of the peptides obtained in step 1 by using four equiv. of the protected Fmoc-amino acid with HBTU (2-(1H-Benzotriazole-1-yl)-1, 1,3,3-tetramethyluronium hexafluorophosphate) as a coupling reagent;
n. suppressing racemization of the peptide obtained in step m by HOBT (n-hydroxybenzotriazole) or COMU (1-Cyano-2-ethoxy-2-oxoethylidenaminooxy)dimethylamino-morpholino-carbenium hexafluorophosphate);
o. confirming the completion of each coupling reaction in step (n) by Kaiser Test,
p. cleaving the peptides obtained in step (o) using TFA cleavage,
q. synthesizing peptides after cleaving the peptides obtained in step (p),
r. purifying to homogeneity the peptides obtained in step (q), using reverse phase HPLC,
s. characterizing the peptides obtained in step (r) by mass spectrometry,
t. in-vitro screening of the peptides obtained in step (s) against hemagglutinin using SAXS based pH experiment.

In a specific embodiment, steps (a) to (j) of the method comprise the process of identifying a "druggable site" in Hemagglutinin protein.

In a specific embodiment, the "druggable site" of Hemagglutinin protein identified in step (j) of the method is useful for screening anti influenza/flu drugs.

In another specific embodiment, the glycosylated HA protein is isolated from strain of influenza virus selected from the group comprising of H1N1, H5N1, H9N2, H3N2 and H14N5.

A person skilled in the art will appreciate that it is possible to employ and use any other strains of influenza virus and using SEQ ID NO. 21-25 as template design and synthesize the peptide sequences that the capable of interacting with influenza hemagglutinin trimeric protein and blocking the pH induced shape change or aggregation of the same

EXAMPLES

The Following Examples are Given Only by Way of Illustration of the Present Invention and Therefore should not be Construed to Limit the Scope of the Present Invention Example 1

Synthesizing and Identifying Peptide Sequences Capable of Binding to Influenza Hemagglutinin Trimeric Protein and Blocking its pH Induced Shape Change The inventors used peptide sequences involved in interchain interaction (SEQ ID 21-25, Table 1) as initial templates for designing peptides capable of binding to this site and blocking pH-induced opening of HA trimer (Table 2). Different combinations of the peptides composing the conserved site is chemically synthesized, purified, characterized and then incubated with HA trimer from H1N1, H5N1, H9N2, H3N2 and H14N5 in a molar ratio of 1:3 (HA trimer:peptide). The incubated trimeric protein is then dialyzed with low pH buffer and their SAXS profile is measured. Importantly, of the twenty peptides screened, eight peptides showed ability to block/retard low pH induced association of the HA proteins. Since the pH induced opening of HA protein is essential for viral entry into host cells, the peptides capable of blocking this process hold potential as anti-influenza molecules.

TABLE 2

| | | | Activity of peptide is represented as: | | | | |
|---|---|---|---|---|---|---|---|
| | | | | in vitro Testing SAXS based activity | | | |
| Peptide | Seq ID | Sequence Details | H1N1 | H3N2 | H5N1 | H9N2 | H14N5 |
| PF11 | 1 | PYDVPDYE | ++ | +++ | ++ | ++ | +++ |
| PF12 | 2 | PYDVPDYA | + | ++ | + | + | ++ |

TABLE 2-continued

Activity of peptide is represented as:

| Peptide | Seq ID | Sequence Details | in vitro Testing H1N1 | H3N2 | SAXS based activity H5N1 | H9N2 | H14N5 |
|---|---|---|---|---|---|---|---|
| PF13 | 3 | PGDFNDYE | ++ | + | ++ | ++ | + |
| PF21 | 9 | GVHHPGTDNDQI | − | + | − | − | + |
| PF22 | 10 | GVHHPSTDSDQT | − | − | − | − | − |
| PF23 | 11 | GVHHPSNETEQR | − | ++ | − | − | ++ |
| PF31 | 4 | TKRSQQTVIP | +++ | ++ | +++ | +++ | ++ |
| PF32 | 5 | TSRSQQTVIP | ++ | ++ | − | ++ | − |
| PF33 | 12 | SSNYNRRFTP | − | − | ++ | − | − |
| PF41 | 6 | KEFSEVEGR | +++ | +++ | +++ | +++ | +++ |
| PF42 | 7 | KEFNNLEKR | ++ | ++ | ++ | ++ | ++ |
| PF51 | 13 | RPKVRDQESR | − | − | − | − | − |
| PF52 | 14 | RPWVRGVSSR | − | − | − | − | − |
| PF53 | 15 | RPWVRGLSSR | − | − | − | − | − |
| PF54 | 16 | RPKVRGQAGR | − | − | − | − | − |
| LPF52 | 17 | GSRPWVRGVSSRIS | − | − | − | − | − |
| LPF54 | 8 | AERPKVRGQAGRMN | − | ++ | − | − | ++ |
| MPF24 | 18 | IWGVAAPGTAAAQI | − | − | − | − | − |
| MPF26 | 19 | IWGVAAPSTASAQTSL | − | − | − | − | − |
| MPF51 | 20 | APAVAAQASA | − | − | − | − | − |

+++: 66-100% inhibition of HA trimer opening relative to no peptide present
++: 33-66% inhibition of HA trimer opening relative to no peptide present
+: 0-30% inhibition of HA trimer opening relative to no peptide present
−: No inhibition of HA trimer opening relative to no peptide present
-PF signifies peptide family; LPF presents long variants whereas MPF represent mutant version of the peptide.

First number in the name represents the family and second number indicates its identity within the family.

The inventors identified eight preferred peptides represented as PF11, PF12, PF13, PF31, PF32, PF41, PF42 and LPF54 showing ability to block pH triggered shape changes in HA proteins from five different viral strains H1N1, H5N1, H9N2, H3N2 and H14N5.

The peptides of the invention and their analogs and variants block the low pH induced opening of HA trimer in a strain independent manner which is essential for fusion of the HA protein with its receptors in the endosome of host cells.

Example 2

Systematic Identification of a Novel Drug Site

The prerequisite for identification of a novel drug site is a template molecule which represents the functionally relevant entity in cellular environment. Due to lack of a physiologically relevant structure of HA trimer, the inventors performed experiments to obtain data to model a physiologically relevant working model of the trimer of HA glycoprotein.

Material and Methods: Glycosylated HA protein excised from surface of H1N1, H5N1, H9N2, H3N2 and H14N5 are purchased from Immune Technology (NY USA). Proteins at concentration close to 1 mg/ml are initially stored in buffer (136 mM NaCl, 2.68 KCl, 1.44 g/l, 10 mM of $Na_2HPO_4$ and $KH_2PO_4$ salts and pH 7.4). The protein is dialyzed with buffers (having same NaCl and KCl amounts): pH 8 (Tris-HCl), pH 7.4, 6.7 and 5.7 (phosphate), 4.7 and 4.4 (acetate). For dialysis, 5 kDa molecular weight cutoff micro dialyzers (Harvard Apparatus) is used. Post-dialysis (five exchanges of 1 hour each), SAXS data is acquired on the protein which provided its shape profile in trimeric closed form and structural evidence on low pH-induced shape change induced aggregation of this protein. SAXS datasets on protein in six different buffers and matched buffers is acquired on the X9 synchrotron beam line of National Synchrotron Light Source, Brookhaven National Laboratory, Upton N.Y. USA. In each experiment, 15 µl of the protein is exposed to the beam of wavelength 0.873 Å.

The samples and their match buffers is exposed for 30 seconds at 15° C. at a flow rate of about 30 µl/min. The acquired SAXS data is scaled and processed to obtain scattering data on proteins using ATSAS suite of programs. Guinier approximations is used to estimate the increase in the dimensions of the scattering species as a function of pH using PRIMUS software (11). Taking cue from dimensions approximated using Guinier analysis, indirect Fourier transformation is done using GNOM45 software (12). Uniform density models for the scattering species is constructed using DAMMIN23IQ software (13) followed by generation of averaged model for best representation of ensemble states of the scattering molecule using DAMAVER suit of programs. The homology model generated from consensus sequence (explained in step 2) is used for comparison with the SAXS based model. The differences between the two models are used as a constraint for glycosylation of the model to get a glycosylated model. Based on SAXS based constraints, in-silico glycosylation using GLYPROT server is performed (14).

Figure 1:
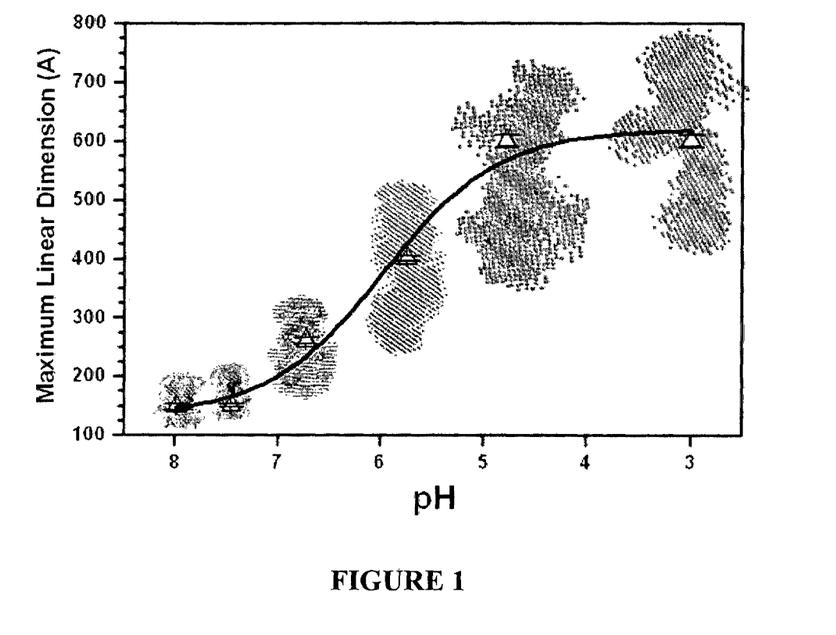
Figure 2:
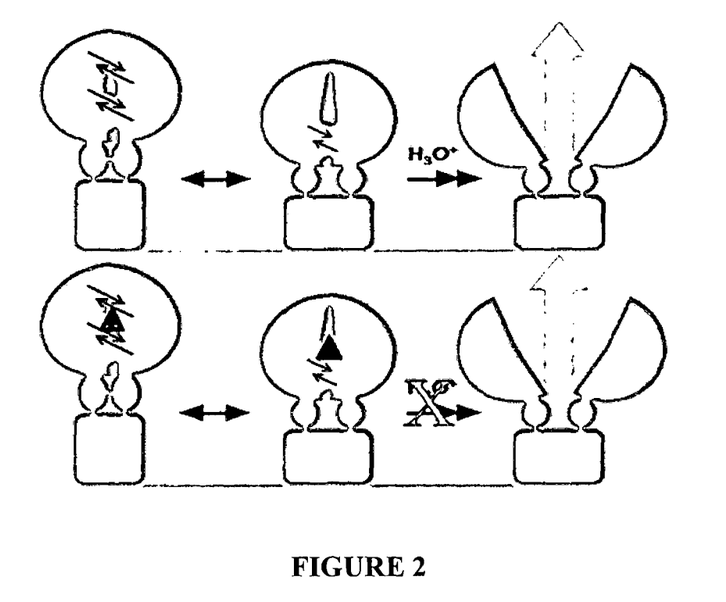
FIG. 2 represents working hypothesis that any molecule including peptides reactive to the conserved druggable site will interfere with the native like behavior of the HA protein and would block pH induced viral entry into host cells. This schematic diagram represents the structural changes which occur in the HA trimer as a function of low pH (upper scheme). Based on known literature, it can be summarized that the envelope protein HA trimer of influenza undergoes dynamic opening and closing in a reversible manner, until it encounters low pH when the equilibrium shifts towards the open structure which allows hydrophobic segments of HA protein to come out. In absence of any detergent in buffer, the hydrophobic portions aggregate as seen in panel A. The lower panel represents our working hypothesis where a small molecule (denoted as a black triangle) reactive to the epitope which is pivotal for dynamic opening and closing of HA protein would interfere with the pH induced opening of HA trimer (lower scheme).
Figure 3:
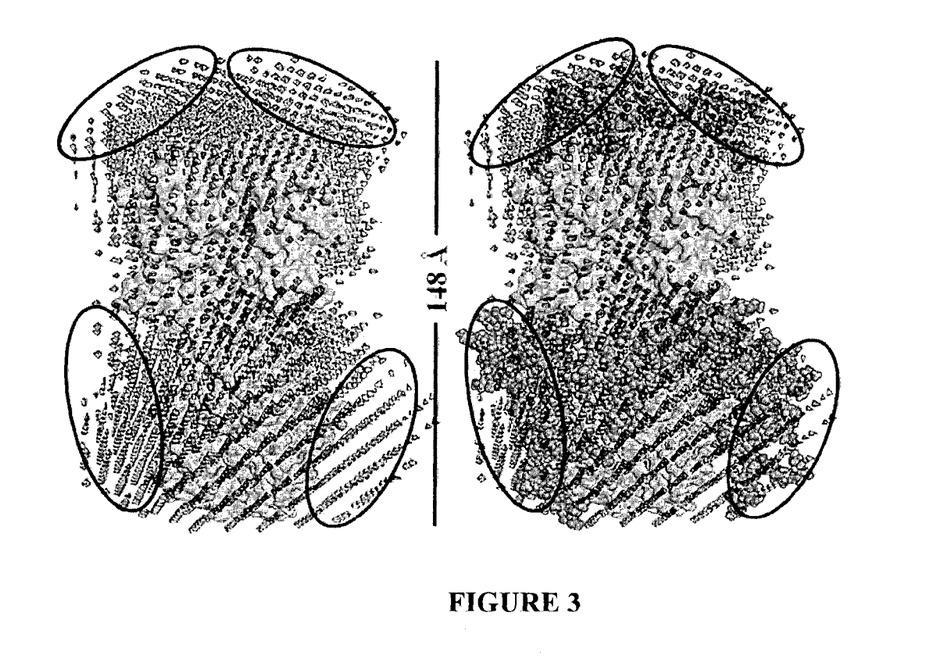
FIG. 3 represents use of SAXS data based models to identify the volumes occupied by the glycosylation in the protein. Left panel represents inertial axis based structural superimposition of the unglycosylated whereas right panel shows glycosylated models of HA with the SAXS based dummy residue model. Here SAXS envelope is shown in black diamonds, homology based model of HA is shown in light grey surface representation and the glycosyl moieties are shown in dark grey cpk representation. Inertial axis based structural superimposition of the unglycosylated (left) and glycosylated (right) models of HA trimer with the SAXS based dummy residue model. The circled zones shown in left shows unoccupied volume whereas in the right show the presence of glycosyl moieties within the SAXS shape.
Figure 4:
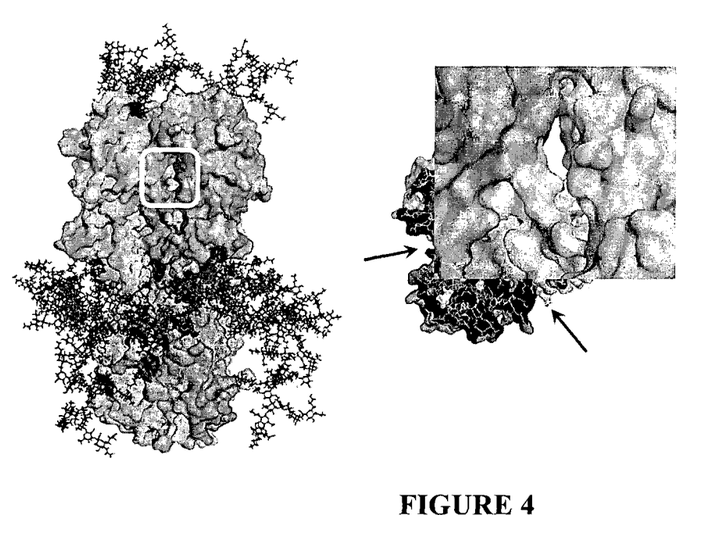

Results and Discussion: The fully glycosylated model for HA trimer is obtained (FIG. 3). The generated model is in good correlation with the SAXS based model and hence is a better and physiologically representative structure of HA protein. SAXS data at low pH confirmed that in absence of detergents in buffer correctly folded HA protein undergoes shape change forms associated forms as shown in FIG. 1. The models shown in the FIG. 1 represent the most probable shape of the scattering species at the defined pH values. These results suggest that above mentioned methodology is fit to be employed to study the low resolution solution structure, to locate sugar moieties in the modeled/crystal structure along with the functionality of HA molecule.

Example 3

Merging Biophysical and Bioinformatics Data to Develop a Residue-Level Resolution Model of Influenza HA Trimer to Identify Druggable Pockets Information from flu database, sequence alignments are merged with the SAXS based low resolution information to obtain a residue-level insight into the model. These experiments provided a structure of influenza HA protein which has remained conserved during evolution regardless of the gene assortments. This model is used for identifying potential druggable pockets.

Materials and Methods: All non redundant, full length pathogenic sequences are collected from FLU database. The dataset is then divided on the basis of time irrespective of the subtype/group to which the HA belongs. The dataset is divided in four groups followed by generation of consensus sequences representing each group. Sequence analysis is performed with these consensus sequences using CLUSTAL software. Based on the alignment, and the sites identified for glycosylation in the model derived from Example 1 with the surface accessible residues (MOLMOL software (15)) and normal mode analysis for inherent disorder and involvement in maintaining interchain interactions in the dynamic opening and closing of HA trimer is done using ELNEMO web server (16), a novel site is identified. The criteria for filtering the novel site included: conserved during evolution, surface exposure, low propensity for glycosylation (confirmed with scattering data based modeling), low inherent disorder, and found to be critical for maintaining chain-chain interaction.

Results and Discussion: The glycosylated model generated in Example 1 is used as template for identification of a novel drug site. The criteria fixed for defining the drug site is defined with a motive that the drug site should be freely available for designing and screening small peptides or molecules. For this, the site is conserved in all the variants of HA protein, the residues comprising the drug site is surface exposed and it should be non-glycosylated, along with these features the site includes residues which are critical for stabilizing the interface of the interacting chains. Based on these features, a novel druggable site is identified in the head group of HA trimer. The drug site identified comprises of SEQ ID NO 21 from chain A and SEQ ID NO 25 from chain B, SEQ ID NO 22 from chain A orients SEQ ID NO 23 towards SEQ ID NO 25 (chain B) and SEQ ID NO 21 (chain A). The SEQ ID NO 23 segment interacts with SEQ ID NO 24 to stabilize the interchain interface. These SEQ ID NOs provide the composition for the identified novel drug site (Table 1). These sequences together form an epitope which represents a druggable site.

Example 4

Chemical Synthesis of Peptides for in vitro Screening

The peptides composing the druggable site, being complementary in nature, reacted back at this site and inhibited in the native-like behavior of the HA protein on sensing the low pH. The sequences of the peptides tested are presented in Table 2.

Materials and Methods: All the peptides are chemically synthesized using standard solid phase peptide synthesis employing (17) Fmoc (N-(9-fluronyl)-methoxycarbonyl), chemistry in 0.02 mmole scale on a Protein Technologies Inc, USA, PS-3 peptide synthesizer. First Fmoc-amino acid (2 equiv.) is anchored on 2-Chlorotrityl chloride resin (substitution 1.01 mmole/g, 100-200 mesh, 1% Di-Vinyl-Benzene (DVB)) manually using diisopropylethylamine (5 equiv.) in dichloromethane. Free 2-Chlorotrityl chloride linkers are capped by treatment of the resin with a solution of dichloromethane/Methanol/diisopropylethylamine (17:2:1; v/v/v) twice and subsequently with a solution of dimethylformamide (DMF)/diisopropylethylamine/acetic anhydride (8:1:1; v/v/v) twice. The resin is washed three times each with dimethyl formamide and dichloromethane respectively and finally dried in vacuum for four hours. Chain elongation of the peptides is done by using four equiv. of the protected Fmoc-amino acid with HBTU (2-(1H-Benzotriazole-1-yl)-1,1,3,3-tetramethyluronium hexafluorophosphate) (4 equivalents) as a coupling reagent and HOBT (n-hydroxybenzotriazole) (18) or COMU (1-Cyano-2-ethoxy-2-oxoethylidenaminooxy)dimethylamino-morpholino-carbenium hexafluorophosphate) (4 equivalents) (19) for suppressing racemization. For F-moc protected amino acids, following side chain protections are employed:—Asparagine, Glutamine, Histidine, Serine: trityl (trt); Glutamine, Aspartic acid: tert-butyl ester (OtBu); Arginine: 2,2,4,6,7-pentamethyldihydrobenzofuran-5-sulfonyl (Pbf); Lysine, Tryptophan: tert-butyloxycarbonyl (Boc); Tyrosine, Threonine: tert-butyl (tbu). For C-terminal activation, 0.4M NMM (N-Methylmorpholine) in DMF is used and for N-terminal Fmoc-group, deprotection 20% piperidine in DMF is used. COMU is used specifically when two or more hydrophobic amino acids occur in succession in the sequence to have better yield. Completion of the reaction is monitored by performing Kaiser Test. After final Fmoc-group removal the peptide is cleaved from the resin by treating the resin with cleavage cocktail containing Trifluoroacetic acid, phenol, water, Thioanisole and 1,2-Ethanedithiol (82.5:5:5:5:2.5; v/v/v/v/v) for 6 hours. Finally it is filtered, dried under air pressure and subsequently on a vacuum to yield 18-20 mg of the crude peptide. Crude peptides are purified by Dionex Ultimate 3000 HPLC on a reverse phase C-18 (4.6×250 mm) column using water/acetonitrile gradient containing 0.1% Trifluoroacetic acid. Organic solvent from the pure eluting fractions is evaporated and the peptides are lyophilized to complete dryness. 10-14 mg of purified peptides is obtained. The purified peptides are characterized with mass spectroscopy.

Results and Discussion: Peptides are synthesized correctly and purified to homogeneity. They are lyophilized after dissolving in acetic acid and stored in −70° C. until use.

Example 5

In-vitro Assay to Test the Effect of Peptides on Global Structure of Hemagglutinin and its pH Dependent Behavior Synthesized peptides are tested for their ability to block low pH induced shape change followed by association of HA proteins. For this experiment, purified HA protein from five different influenza strains is purchased.

Materials and Methods: Purified peptides are dissolved in Tris buffer pH 8. The stock solution of the peptides are mixed with HA proteins in 3:1 molar ratio ([peptide]:[HA trimer]). The rationale for considering this ratio is that each HA trimer have three putative binding sites/pockets and the inventors wanted the peptides to saturate all possible/available binding sites. After incubation of 2 hours with mixing, the mixture is dialyzed against buffers with varying pH but same ionic strength using micro-dialyzers (as described in Example 1). Aliquots are drawn at each pH point and SAXS data is acquired from the sample, and analyzed for the shape parameters of the predominant scattering species in solution.

Figure 5:
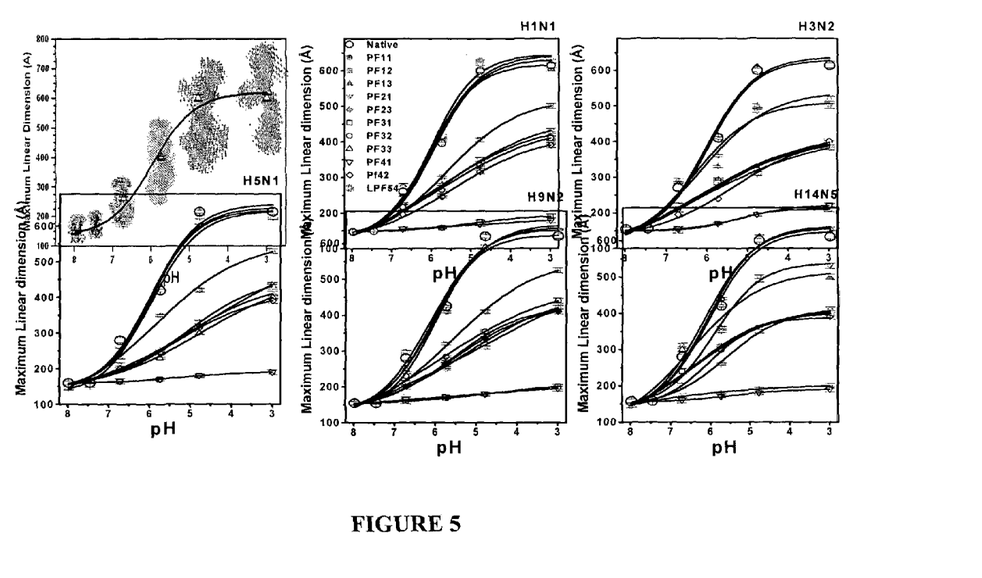
FIG. 5 presents the variation in the L values of the scattering particles (indicator of association of HA molecules incubated with peptides) as a function of buffer pH. Graph showing pH dependent association of HA alone and in presence of inhibitory peptides. Top left panel shows the change in length at different pH values of H1N1-HA. Other graphs in this figure present the comparative ability of different peptides to block pH dependent opening of the HA trimer in solution conditions using SAXS.

Results and Discussion: Measured SAXS data is analyzed using Guinier Approximation (using PRIMUS package) to estimate the radius of gyration ($R_G$) and cross-sectional radius ($R_C$) of the scattering species. These values are used to estimate the linear dimension (L) of the scattering species (in this case, unassociated or associated from of HA protein trimers; peptides being too small in mass do not contribute detectably in mixture). Formula for estimation of L was L=SQRT $(12((R_G^2)-(R_C^2)))$. The estimated L values from mixtures are plotted as a function of solution pH. This brought forth that of the twenty peptides tested, eight peptides showed ability to block pH induced association of HA protein from different viral strains. Table 2 and FIG. 5 represent the in vitro activity of peptides with hemagglutinin of different viral strains.

Advantages of the Invention

1. The peptides of the invention target the novel drug site in hemagglutinin trimer in a strain independent manner.
2. The invention provides a novel druggable site common to all known pathogenic strains of influenza and can be utilized for developing anti-influenza/Flu drugs.
3. The invention overcomes the limitations of crystallographic technique based structural insights to provide a better working model of influenza HA trimer for drug development and screening.
4. The invention describes peptides sequences which can inhibit pH-induced association of HA protein from different strains.

BIBLIOGRAPHY

1. Wang, T. T., and Palese, P. (2009) *Cell* 137, 983-985
2. Harrison, S. C. (2008) *Nat Struct Mol Biol* 15, 690-698
3. Bullough, P. A., Hughson, F. M., Skehel, J. J., and Wiley, D. C. (1994) *Nature* 371, 37-43
4. Bodian, D. L., Yamasaki, R. B., Buswell, R. L., Stearns, J. F., White, J. M., and Kuntz, I. D. (1993) *Biochemistry* 32, 2967-2978
5. Ruigrok, R. W., Wrigley, N. G., Calder, L. J., Cusack, S., Wharton, S. A., Brown, E. B., and Skehel, J. J. (1986) *EMBO J* 5, 41-49
6. Kielian, M., and Rey, F. A. (2006) *Nat Rev Microbiol* 4, 67-76
7. Chen, J., Lee, K. H., Steinhauer, D. A., Stevens, D. J., Skehel, J. J., and Wiley, D. C. (1998) *Cell* 95, 409-417
8. Brandenburg, B., and Zhuang, X. (2007) *Nat Rev Microbiol* 5, 197-208
9. Chen, H., Cheung, C. L., Tai, H., Zhao, P., Chan, J. F., Cheng, V. C., Chan, K. H., and Yuen, K. Y. (2009) *Emerg Infect Dis* 15, 1970-1972
10. Cheng, P. K., Leung, T. W., Ho, E. C., Leung, P. C., Ng, A. Y., Lai, M. Y., and Lim, W. W. (2009) *Emerg Infect Dis* 15, 966-968
11. Konarev, P. V., Volkov, V. V., Sokolova, A. V., Koch, M. H. J., and Svergun, D. I. (2003) *Journal of Applied Crystallography* 36, 1277-1282
12. Svergun, D. I. (1992) *Journal of Applied Crystallography* 25, 495-503
13. Volkov, V. V., and Svergun, D. I. (2003) *Journal of Applied Crystallography* 36, 860-864
14. Bohne-Lang, A., and von der Lieth, C. W. (2005) *Nucleic Acids Res* 33, W214-219
15. Koradi, R., Billeter, M., and Wuthrich, K. (1996) *Journal of Molecular Graphics* 14, 51-&
16. Suhre, K., and Sanejouand, Y. H. (2004) *Nucleic Acids Res* 32, W610-614
17. Albericio, F. (2000) *Solid-Phase Synthesis: A practical Guide* (1 Ed), CRC Press,
18. Fields, C. G., Lloyd, D. H., Macdonald, R. L., Otteson, K. M., and Noble, R. L. (1991) *Pept Res* 4, 95-101
19. El-Faham, A., Subiros Funosas, R., Prohens, R., and Albericio, F. (2009) *Chemistry Eur J* 15, 9404-9416

The invention claimed is:

1. An isolated peptide capable of binding with any of the peptide sequence of influenza hemagglutinin (HA) protein represented by SEQ ID NOs: 21-25 and blocking pH-induced shape change or aggregation of the influenza hemagglutinin (HA) protein, wherein the peptide is selected from the group consisting of peptides represented by SEQ ID NOs: 1 and 3-8, and wherein the peptide acts in a strain independent manner.

2. An isolated peptide for use in blocking pH-induced shape change or aggregation of the influenza hemagglutinin (HA) protein, wherein the peptide is selected from the group consisting of peptides represented by SEQ ID NOs: 1 and 3-8 and wherein the peptide acts in a strain independent manner and is capable of binding with any of the peptide sequence of influenza hemagglutinin (HA) protein represented by SEQ ID NOs: 21-25.

3. The peptide as claimed in claim 1, wherein the peptide blocks the low pH-induced opening of influenza hemagglutinin (HA) trimer protein.

4. The peptide as claimed in claim 1 or claim 2, wherein the peptide is a synthetic peptide.

5. A composition comprising the peptide as claimed in claim 1 or claim 2 further comprising pharmaceutically acceptable additives and carriers.

6. An influenza vaccine comprising the peptide as claimed in claim 1 or claim 2 as an active ingredient.

7. A kit comprising the peptide as claimed in claim 1 or claim 2 for treatment of diseases caused by influenza virus along with an instructions manual and optionally along with additives and carriers.

8. A method of treatment of diseases caused by influenza virus, said method comprising administering to the subject in need therefore an effective amount of the peptide as claimed in claim 1 or claim 2 or a composition or conjugate comprising said peptide.

9. The method as claimed in claim 8, wherein the peptide is delivered using biodegradable nanoparticles.

10. The method as claimed in claim 8, wherein the peptide is administered by intravenous, intramuscular, spinal, epidural, transdermal, subcutaneous, parenteral, intranasal, mucosal, oral or rectal route.

11. The method as claimed in claim 8, wherein the peptide is effective in the treatment of subjects selected from the group consisting of humans, captive animals, birds and poultry.

12. The method as claimed in claim 8, wherein the peptide is used singly or in combination.

13. An isolated nucleotide sequence encoding the amino acid sequence of the peptide as claimed in claim 1 or claim 2.

14. A vector comprising the nucleotide sequence as claimed in claim 13.

* * * * *